(12) United States Patent
Zanon et al.

(10) Patent No.: US 7,608,711 B2
(45) Date of Patent: Oct. 27, 2009

(54) PROCESS FOR THE PREPARATION OF ZIPRASIDONE

(75) Inventors: Jacopo Zanon, Venice (IT); Oscar Martini, Bollate (IT); Francesco Ciardella, Padua (IT); Luca Gregori, Peraga di Vigonza (IT); Federico Sbrogio, Montecchio Maggiore (IT); Andrea Castellin, Mestrino (IT)

(73) Assignee: Dipharma Francis Srl, Baranzate (Milan) (IT)

( * ) Notice: Subject to any disclaimer, the term of this patent is extended or adjusted under 35 U.S.C. 154(b) by 302 days.

(21) Appl. No.: 11/595,861

(22) Filed: Nov. 13, 2006

(65) Prior Publication Data

US 2007/0117810 A1    May 24, 2007

(30) Foreign Application Priority Data

Nov. 18, 2005    (IT)    ............ MI2005A2216

(51) Int. Cl.
*C07D 417/12*    (2006.01)
*C07D 209/34*    (2006.01)
(52) U.S. Cl. .................... 544/368; 548/486
(58) Field of Classification Search ............ None
See application file for complete search history.

(56) References Cited

U.S. PATENT DOCUMENTS

| | | | |
|---|---|---|---|
| 4,831,031 A * | 5/1989 | Lowe et al. ............ | 514/254.02 |
| 2005/0282819 A1 * | 12/2005 | Graham et al. ......... | 514/254.04 |
| 2006/0089502 A1 * | 4/2006 | Venkataraman et al. ..... | 544/368 |

\* cited by examiner

*Primary Examiner*—Emily Bernhardt
(74) *Attorney, Agent, or Firm*—Young & Thompson

(57) ABSTRACT

A process for the preparation of ziprasidone and a novel intermediate useful in its preparation. The process comprises the reduction of a compound (III) to give a compound (V) which is then reduced to compound (II). This is reacted with compound (IV) to give the desired compound.

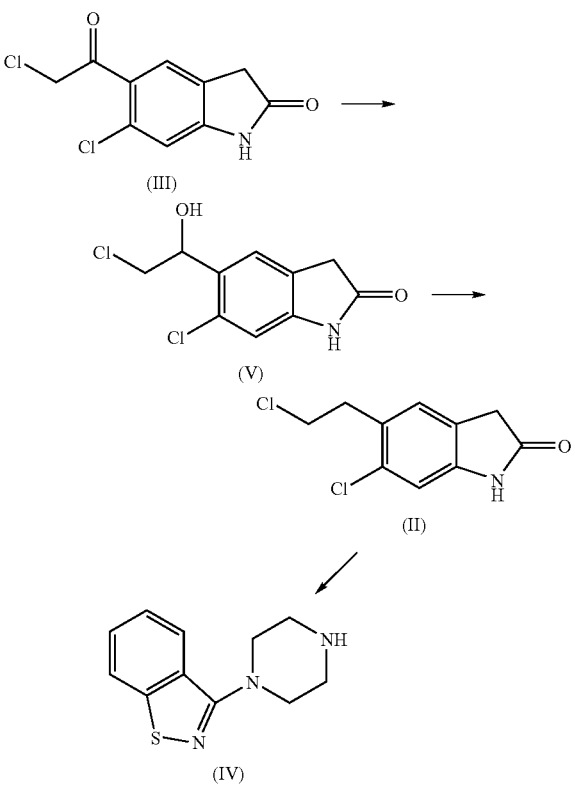

5 Claims, No Drawings

PROCESS FOR THE PREPARATION OF ZIPRASIDONE

FIELD OF THE INVENTION

The present invention relates to a novel process for the preparation of ziprasidone, 5-(2-(4-benzo[d]isothiazol-3-yl)piperazin-1-yl)ethyl)-6-chloro-1,3-dihydro-2H-indol-2-one, and a novel intermediate useful for its preparation.

TECHNOLOGICAL BACKGROUND

Ziprasidone, of formula (I)

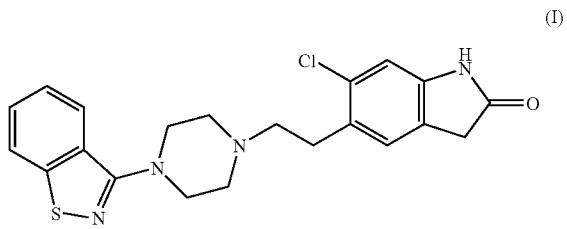

(I)

is an antipsychotic drug known from U.S. Pat. No. 4,831,031. The process for the preparation of ziprasidone disclosed in U.S. Pat. No. 4,831,031 comprises the formation of a compound (II) by reduction of a compound (III) and subsequent reaction with a compound (IV), according to the following scheme:

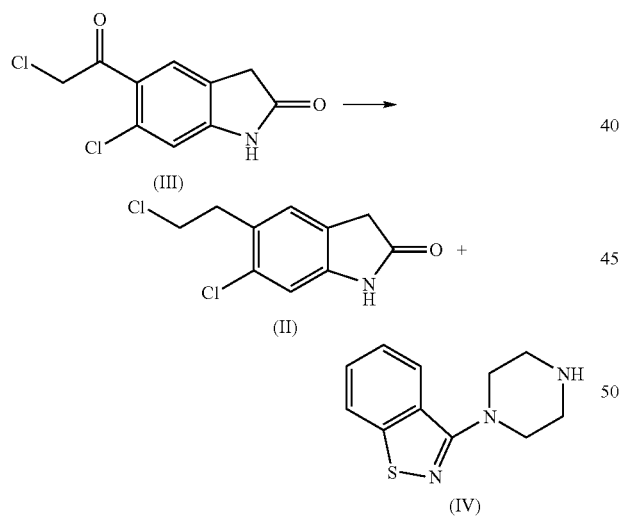

The reduction of a compound (III) to form a compound (II) is carried out by reaction with trifluoroacetic acid and triethylsilane, which are very expensive, thus remarkably affecting the product cost. Chloroketone (III) is an eye irritant and its presence, even in traces, as an impurity in intermediate (II) and in the final product, is a problem for operators. Moreover, said impurity reacts with a compound (IV) to form a further impurity (A), 5-(2-(4-benzo[d]isothiazol-3-yl)piperazin-1-yl)acetyl)-6-chloro-1,3-dihydro-2H-indol-2-one, which is present in the final product and is difficult to remove.

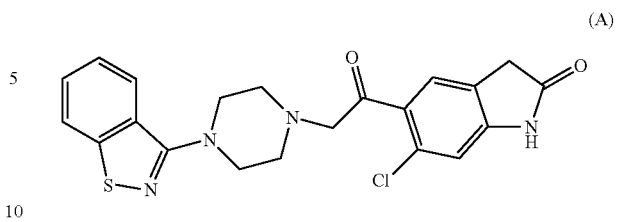

(A)

The drawbacks of the process according to U.S. Pat. No. 4,831,031 are thus evident. There is therefore the need for an improved process for the preparation of zipresidone which is less expensive and free from the drawbacks of the known methods.

SUMMARY OF THE INVENTION

An improved process for the preparation ziprasidone has now been found, in which the amounts of expensive reducing agents used are remarkably lowered. In particular, the content in chloroketone (III) and in impurity (A) in the final product is remarkably lowered.

DETAILED DISCLOSURE OF THE INVENTION

A first object of the invention is a process for the preparation of ziprasidone (I) or a pharmaceutically acceptable salt thereof,

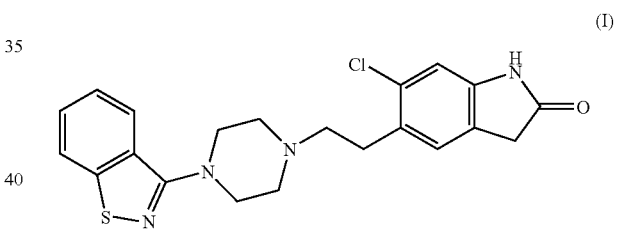

(I)

which comprises
a) reducing a compound (III)

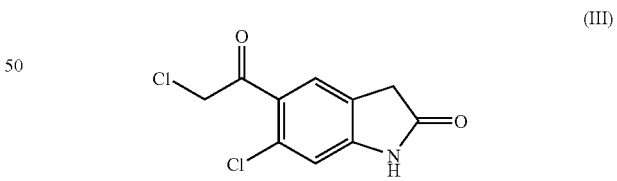

(III)

to yield a compound (V)

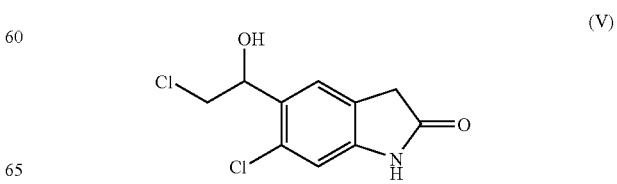

(V)

b) reducing compound (V) to yield a compound (II)

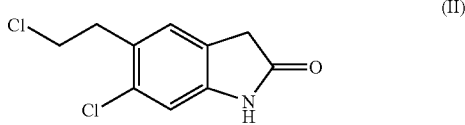

c) reacting compound (II) with a compound (IV)

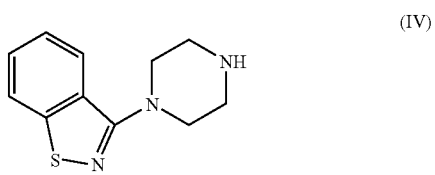

d) and, if desired, converting compound (I) to a pharmaceutically acceptable salt thereof.

A compound (I) can be salified with an organic or inorganic acid, as disclosed in U.S. Pat. No. 4,831,031, optionally in the hydrate form, typically as the mono-, di- or tri-hydrate (U.S. Pat. No. 4,831,031, U.S. Pat. No. 5,312,925 and US 2004/0048876).

A compound (III) can be reduced for example by treatment with an alkali metal borohydride, in particular sodium or lithium, preferably sodium borohydride. The reaction can be carried out in a solvent selected from e.g. water; a $C_1$-$C_4$ alkanol, typically methanol, ethanol, propanol, isopropanol, n-butanol; aliphatic cyclic and alicyclic ethers; glycols or derivatives thereof, typically diethyl ether, diisopropyl ether, methyl tert-butyl ether, tetrahydrofuran, 2-methyltetrahydrofuran and methoxyethyl glycol; and acetic acid; at a temperature approx. ranging from 0 to 60° C., preferably from 20 to 40° C.

Subsequently, a compound (V) can be reduced by treatment with trifluoroacetic acid and triethylsilane, according to known methods.

Compound (V), 6-chloro-5-(2-chloro-1-hydroxy-ethyl)-1,3-dihydro-indol-2-one, in particular in crystalline form, is novel and is an object of the invention.

The reaction between a compound (II) and a compound (IV) can be carried out for example as disclosed in U.S. Pat. No. 4,831,031. The reaction is preferably carried out in homogeneous phase, typically in dimethylsulfoxide, for a time approx. ranging from 1 to 24 hours, preferably from 6 to 15 hours, at a temperature approx. ranging from 90 to 110° C., preferably from 95 to 100° C. The conversion of a compound (I) to a pharmaceutically acceptable salt thereof and/or its preparation in the hydrate form can be carried out according to known methods.

According to the process of the invention, the reduction of a compound (III) is carried out in two steps, via formation of a compound (V), thereby remarkably reducing the necessary amount of trifluoroacetic acid/triethylsilane, a very expensive reducing agent, which is in fact replaced by the much more economic alkali metal borohydride. The two-step reduction of a compound (III) to a compound (II), and the different solvent solubility of the isolated halohydrin (V), compared with a chloroketone (III), surprisingly reduces the presence of the latter as an impurity in intermediate (II) and in the final product to an amount not greater than about 500 ppm, typically not greater than about 100 ppm. As a consequence, compound (A), 5-(2-(4-benzo[d]isothiazol-3-yl)piperazin-1-yl)acetyl)-6-chloro-1,3-dihydro-2H-indol-2-one is present in the final product as an impurity in amounts not greater than about 500 ppm, typically not greater than about 100 ppm.

The invention therefore provides a process for the preparation of ziprasidone, or a pharmaceutically acceptable salt thereof, containing 5-(2-(4-benzo[d]isothiazol-3-yl)piperazin-1-yl)acetyl)-6-chloro-1,3-dihydro-2H-indol-2-one in amounts not greater than about 500 ppm; preferably not greater than about 100 ppm, and if the case a chloroketone (III) in amounts not greater than about 500 ppm, preferably not greater than about 100 ppm.

An object of the invention is also a pharmaceutical composition comprising a carrier and/or excipient and, as the active ingredient, ziprasidone or a pharmaceutically acceptable salt thereof, containing 5-(2-(4-benzo[d]isothiazol-3-yl)piperazin-1-yl)acetyl)-6-chloro-1,3-dihydro-2H-indol-2-one in amounts not greater than about 500 ppm, preferably not greater than about 100 ppm, and if the case a chloroketone (III) in amounts not greater than about 500 ppm, preferably not greater than about 100 ppm.

The pharmaceutical composition of the invention can be prepared according to known methods and used in therapy for the treatment of those pathologies in which ziprasidone or a ziprasidone salt is used, for example schizophrenia. The daily dosage of ziprasidone can usually range from about 0.5 mg to about 500 mg; preferably from 20 to 80 mg, in a single or repeated daily administrations.

The following examples illustrate the invention.

Example 1

6-Chloro-5-(2-chloro-1-hydroxy-ethyl)-1,3-dihydro-indol-2-one. (V)

A reactor is loaded with 200 g (0.82 mol) of 6-chloro-5-(2-chloro-acetyl)-1,3-dihydro-indol-2-one, in 1 L of ethanol. The reaction mixture is added with 15.5 g (0.41 mol) of sodium borohydride in portions, under strong stirring, at room temperature. The temperature is kept at 15-20° C. during the addition, after that the mixture is left under stirring for about 15 h at room temperature. The mixture is then added with 250 ml of glacial acetic acid and refluxed (approx. 85° C.) for 1 hr 30 min, then 200 ml of acetic acid are added and the mixture is refluxed a further 30 min, then cooled to 20° C. The suspension is filtered and washed with ethanol and heptane. The solid product is dried under vacuum at a temperature of 60° C., to obtain 177 g (88% molar yield).

Purification of 6-Chloro-5-(2-chloro-1-hydroxy-ethyl)-1,3-dihydro-indol-2-one. (V)

A reactor is loaded with 25 g of 6-chloro-5-(2-chloro-1-hydroxy-ethyl)-1,3-dihydro-indol-2-one suspended in 100 ml of acetone. The mixture is refluxed for about 1 h, then the suspension is cooled at room temperature, stirring for a further 30 min under nitrogen atmosphere.

The mixture is filtered under inert atmosphere, to obtain 26.4 g of a white solid, which is dried for 12 h under vacuum at 40° C., to afford 22.6 g of a crystalline white solid.

$^1$H NMR, dmso-d6, 300 MHz (δ ppm, J Hz): 10.50 (1H, s, H1); 7.42 (1H, s, H7); 6.80 (1H, s, H4); 5.95 (d, J=4.9, OH); 5.04 (1H, m, J=3.8, H5'); 3.71 (1H, dd, J=11.2, J=3.8, H5"); 3.58 (1H, m, J=3.8, H5'); 3.71 (1H, dd, J=11.2, J=3.8, H5"); 3.34 (1H, s, H3).

$^{13}$C NMR, dmso-d6, 75 MHz (δppm): 177.2; 145.1; 132.5; 130.5; 126.1; 124.8; 70.0; 49.9; 36.3.

Example 2

6-Chloro-5-(2-chloro-ethyl)-1,3-dihydro-indol-2-one. (II)

A 2 L round-bottom flask is loaded with 300 g (1.22 mols) of 6-chloro-5-(2-chloro-1-hydroxy-ethyl)-1,3-dihydro-indol-2-one and 1140 ml of trifluoroacetic acid, under nitrogen atmosphere. The mixture is stirred at room temperature for 1 h, then heated to about 35-40° C. 214 ml (1.34 mols) of triethylsilane are then dropped therein in approx. 1 hr 30 min, keeping stirring for 12-14 h. Separately, a round-bottom flask is loaded with 3000 g of a water/ice mixture and the reaction mixture is carefully dropped therein, in about 1 hr 30 min, under strong stirring. The resulting white suspension is stirred for 30 min, then filtered, washed with purified water (4×500 ml) and heptane (400 ml), then dried at 60° C. under vacuum to afford 281 g of 6-chloro-5-(2-chloro-ethyl)-1,3-dihydro-indol-2-one.

Example 3

5-(2-(4-Benzo[d]isothiazol-3-yl)piperazin-1-yl)ethyl)-6-chloro-1,3-dihydro-2H-indol-2-one hydrochloride. (I)

A reactor is loaded with 131 g (0.57 mol) of 6-chloro-5-(2-chloro-ethyl)-1,3-dihydro-indol-2-one, 125 g (0.57 mol) of piperazinyl benzoisothiazole, 260 ml of dimethylsulfoxide, 26 ml of water and 4.3 g (0.0285 mols) of NaI. The reaction mixture is added with 103 g (0.969 mol) of $Na_2CO_3$, with stirring under nitrogen atmosphere. The resulting mixture is heated to about 115-125° C. in 1 h and kept at said temperature under stirring for approx. 1 hr 45 min, then cooled and slowly added in about 25 min with isopropyl alcohol (650 ml), at a temperature of about 110° C., then slowly cooled at 25° C. The filtrate and the precipitate are washed with isopropyl alcohol (2×130 ml) to obtain 310 g of 5-(2-(4-benzo[d]isothiazol-3-yl) piperazin-1-yl)ethyl)-6-chloro-1,3-dihydro-2H-indol-2-one free base, as a crystalline solid. The resulting product is placed in a 3 L beaker with 1500 ml of purified water, and 150 ml of 32% HCl are dropped therein with stirring. The reaction mixture is kept under stirring for 10 min, filtered, washed with purified water (2×500), dried to give 260 g of 5-(2-(4-benzo[d]isothiazol-3-yl) piperazin-1-yl)ethyl)-6-chloro-1,3-dihydro-2H-indol-2-one hydrochloride, as a crystalline solid.

Example 4

5-(2-(4-Benzo[d]isothiazol-3-yl)piperazin-1-yl)ethyl)-6-chloro-1,3-dihydro-2H-indol-2-one. (I)

A reactor is loaded with 200 g (0.86 mol) of 6-chloro-5-(2-chloro-eythyl)-1,3-dihydro-indol-2-one, 191 g (0.87 mol) of piperazinyl benzoisothiazole, 92 g (0.87 mols) of $Na_2CO_3$, 400 ml of dimethylsulfoxide and 40 ml of water. The resulting mixture is heated to about 95-100° C. and kept at said temperature under stirring for approx. 6-12 h, then the hot suspension is slowly added with isopropyl alcohol (1000 ml) in about 25 min, and finally slowly cooled to 20° C. The precipitate is filtered and washed with isopropyl alcohol (2×100 ml). The resulting product is placed in a 3 L beaker with 1300 ml of purified water and the resulting mixture is kept under stirring for 30 min at 30-35° C. The suspension is filtered, washed with purified water (640 ml) and methanol (160 ml×4 times) and dried to afford 260 g of 5-(2-(4-benzo[d]isothiazol-3-yl)piperazin-1-yl)ethyl)-6-chloro-1,3-dihydro-2H-indol-2-one, as a crystalline solid, in a 72% molar yield.

The invention claimed is:

1. A process for the preparation of ziprasidone (I) or a pharmaceutically acceptable salt thereof,

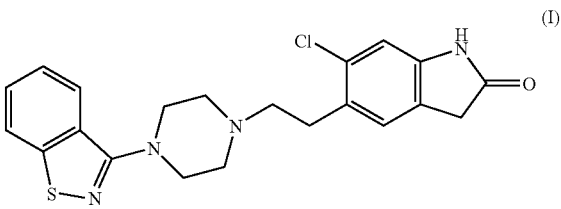

which comprises a) reducing a compound (III)

by treatment with an alkali metal borohydride to yield a compound (V)

b) reducing compound (V) to yield a compound (II)

c) reacting compound (II) with a compound (IV)

d) and, if desired, converting compound (I) to a pharmaceutically acceptable salt thereof.

2. The process as claimed in claim 1, wherein the reduction of a compound (III) is carried out in a solvent selected from water, a $C_1$-$C_4$ alkanol, aliphatic cyclic or alicyclic ethers, glycols, and acetic acid.

3. The process as claimed in claim 1, wherein a compound (III) is reduced by treatment with sodium borohydride in ethanol.

4. The process as claimed in claim 1, wherein the reaction between a compound (II) and a compound (IV) is carried out in homogeneous phase.

5. The process as claimed in claim 4, wherein the reaction is carried out in dimethylsulfoxide, at a temperature approx. ranging from 90 to 110° C.

* * * * *